United States Patent
Ishiwata

(10) Patent No.: US 10,563,177 B2
(45) Date of Patent: Feb. 18, 2020

(54) EVALUATING A PLURIPOTENT STEM CELL BASED ON A REGION OF A PHASE DISTRIBUTION IMAGE HAVING A PHASE AMOUNT LESS THAN A THRESHOLD PHASE AMOUNT OF A MITOCHONDRION IN A SOMATIC CELL

(71) Applicant: OLYMPUS CORPORATION, Hachioji-shi, Tokyo (JP)

(72) Inventor: Hiroshi Ishiwata, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 141 days.

(21) Appl. No.: 15/631,831

(22) Filed: Jun. 23, 2017

(65) Prior Publication Data
US 2018/0002670 A1    Jan. 4, 2018

(30) Foreign Application Priority Data

Jun. 29, 2016 (JP) .................................. 2016-128881

(51) Int. Cl.
| | | |
|---|---|---|
| *C12N 5/074* | (2010.01) | |
| *G01N 15/14* | (2006.01) | |
| *G06T 7/11* | (2017.01) | |
| *G06T 7/168* | (2017.01) | |
| *G06T 7/50* | (2017.01) | |
| *G01N 33/483* | (2006.01) | |
| *G06T 7/00* | (2017.01) | |
| *G01N 15/10* | (2006.01) | |

(52) U.S. Cl.
CPC ........... *C12N 5/0696* (2013.01); *G01N 15/14* (2013.01); *G01N 15/1434* (2013.01); *G01N 15/1475* (2013.01); *G01N 33/4833* (2013.01); *G06T 7/0012* (2013.01); *G06T 7/11* (2017.01); *G06T 7/168* (2017.01); *G06T 7/50* (2017.01); *G01N 2015/1006* (2013.01); *G01N 2015/1454* (2013.01); *G06T 7/00* (2013.01); *G06T 2207/10056* (2013.01); *G06T 2207/30004* (2013.01); *G06T 2207/30024* (2013.01)

(58) Field of Classification Search
None
See application file for complete search history.

(56) References Cited

U.S. PATENT DOCUMENTS

| | | |
|---|---|---|
| 2012/0057013 A1 | 3/2012 | Ishiwata |
| 2014/0285650 A1 | 9/2014 | Ishiwata |

FOREIGN PATENT DOCUMENTS

| | | | |
|---|---|---|---|
| JP | 2011229409 | * 11/2011 | ............ C12M 41/14 |
| JP | 2011229409 A | 11/2011 | |
| JP | 2012073591 A | 4/2012 | |
| JP | 2014209085 A | 11/2014 | |

OTHER PUBLICATIONS

Wang, Zhuo, et al. "Label-free intracellular transport measured by spatial light interference microscopy." Journal of Biomedical Optics 16.2 (2011): 026019.*
Suhr, Steven T., et al. "Mitochondrial rejuvenation after induced pluripotency." PloS one 5.11: e14095. (Year: 2010).*

* cited by examiner

*Primary Examiner* — G Steven Vanni
(74) *Attorney, Agent, or Firm* — Holtz, Holtz & Volek PC

(57) ABSTRACT

An operation device includes: a communication unit that receives signals of images of a biological sample and outputs data to a display medium, the images being captured by a microscope that converts a phase distribution into an image intensity distribution; and a calculator that calculates a first phase distribution of the biological sample from the image signals. The calculator extracts a region having a phase amount that is not less than a specified phase amount from the first phase distribution, and generates evaluation information by using the region having a phase amount that is not less than the specified phase amount, that is an indicator used when a user evaluates a state of the biological sample; and the communication unit outputs the evaluation information to the display medium.

15 Claims, 13 Drawing Sheets

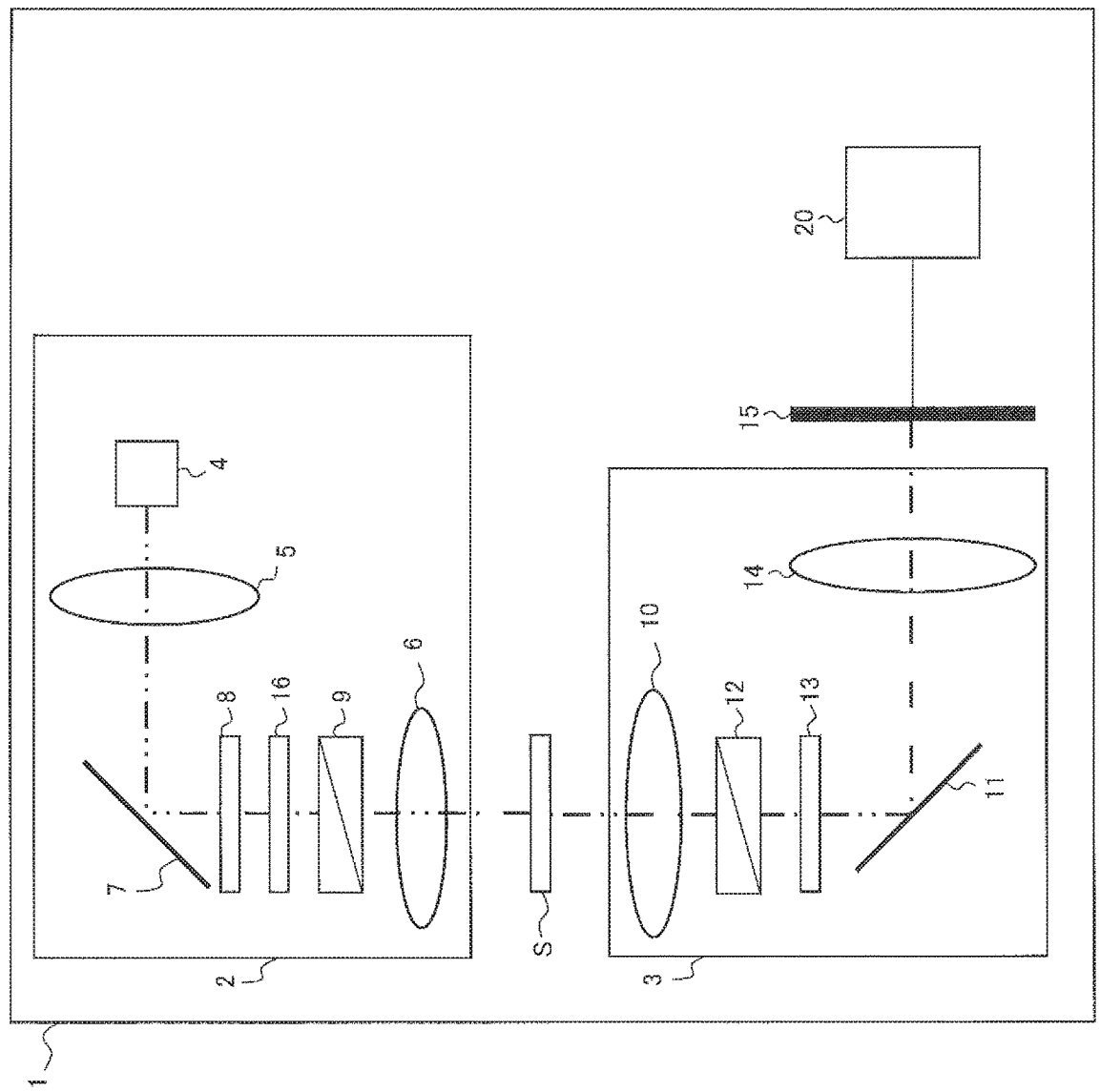
F I G. 1

EVALUATING A PLURIPOTENT STEM CELL BASED ON A REGION OF A PHASE DISTRIBUTION IMAGE HAVING A PHASE AMOUNT LESS THAN A THRESHOLD PHASE AMOUNT OF A MITOCHONDRION IN A SOMATIC CELL

CROSS REFERENCE TO RELATED APPLICATIONS

This application is based upon and claims the benefit of priority from prior Japanese Patent Application No. 2016-128881, filed Jun. 29, 2016, the entire contents of which are incorporated herein by this reference.

BACKGROUND OF THE INVENTION

Field of the Invention

The present invention relates to a method for assisting in evaluating a pluripotent stem cell without stains using a phase distribution of the pluripotent stem cell, a storage medium, and an operation device.

Description of the Related Art iPS cells (induced pluripotent stem cells) and ES cells (embryonic stem cells) have been attracting attention in the field of regeneration medicine in which, for example, a live organ transplant is dealt with, because these cells are pluripotent against various tissues.

On the other hand, in the process of culturing an iPS cell, an iPS cell may be mutated due to, for example, a change in the culture environment or a cell division phase. A cell obtained by an iPS cell being mutated is not pluripotent, wherein a function as an iPS cell is lost. Thus, in order to selectively extract an iPS cell in a good state, it is important to know how to identify a mutated cell. Conventionally, a technology is known that estimates a state of a cell, taking into consideration an identification of a mutated cell.

For example, Japanese Laid-open Patent Publication No. 2011-229409 discloses a technology that extracts a change in a morphological feature amount such as a size or an outer perimeter of a colony in an iPS cell and a feeder cell, and specifies, from among the feature amounts, a feature amount in which information on the iPS cell is reflected, so as to estimate a state of the iPS cell.

Japanese Laid-open Patent Publication No. 2014-209085 discloses a technology that calculates a precise phase distribution of a phase object, such as a cell, that has a three-dimensional structure by reducing a defocused image component and extracting only information situated near a focal point, so as to accurately investigate a three-dimensional structure of a cell or a tissue without stains.

SUMMARY OF THE INVENTION

A method for assisting in evaluating a pluripotent stem cell without stains according to an aspect of the present invention includes: calculating a first phase distribution of a biological sample from signals of images of the biological sample, the images being captured by a microscope that converts a phase distribution into an image intensity distribution; extracting a region having a phase amount that is not less than a specified phase amount from the first phase distribution; and generating evaluation information by using the region having a phase amount that is not less than the specified phase amount, that is an indicator used when a user evaluates a state of the biological sample, and presenting the evaluation information, wherein the specified phase amount is a phase amount of a mitochondrion in a somatic cell.

A non-transitory storage medium according to an aspect of the present invention has stored therein a program that causes a computer to execute a process including: receiving signals of images of a biological sample, the images being captured by a microscope that converts a phase distribution into an image intensity distribution; calculating a first phase distribution of the biological sample from the image signals; extracting a region having a phase amount that is not less than a specified phase amount from the first phase distribution; and generating evaluation information by using the region having a phase amount that is not less than the specified phase amount, that is an indicator used when a user evaluates a state of the biological sample, and outputting the evaluation information, wherein the specified phase amount is a phase amount of a mitochondrion in a somatic cell.

An operation device according to an aspect of the present invention includes: a communication unit that receives signals of images of a biological sample and outputs data to a display medium, the images being captured by a microscope that converts a phase distribution into an image intensity distribution; and a calculator that calculates a first phase distribution of the biological sample from the image signals, wherein the calculator extracts a region having a phase amount that is not less than a specified phase amount from the first phase distribution, and generates evaluation information by using the region having a phase amount that is not less than the specified phase amount, that is an indicator used when a user evaluates a state of the biological sample; the communication unit outputs the evaluation information to the display medium; and the specified phase amount is a phase amount of a mitochondrion in a somatic cell.

BRIEF DESCRIPTION OF THE DRAWINGS

The present invention will be more apparent from the following detailed description when the accompanying drawings are referenced.

FIG. 1 illustrates a configuration of a microscope and an operation device according to a first embodiment;

DESCRIPTION OF THE EMBODIMENTS

Figure 2:
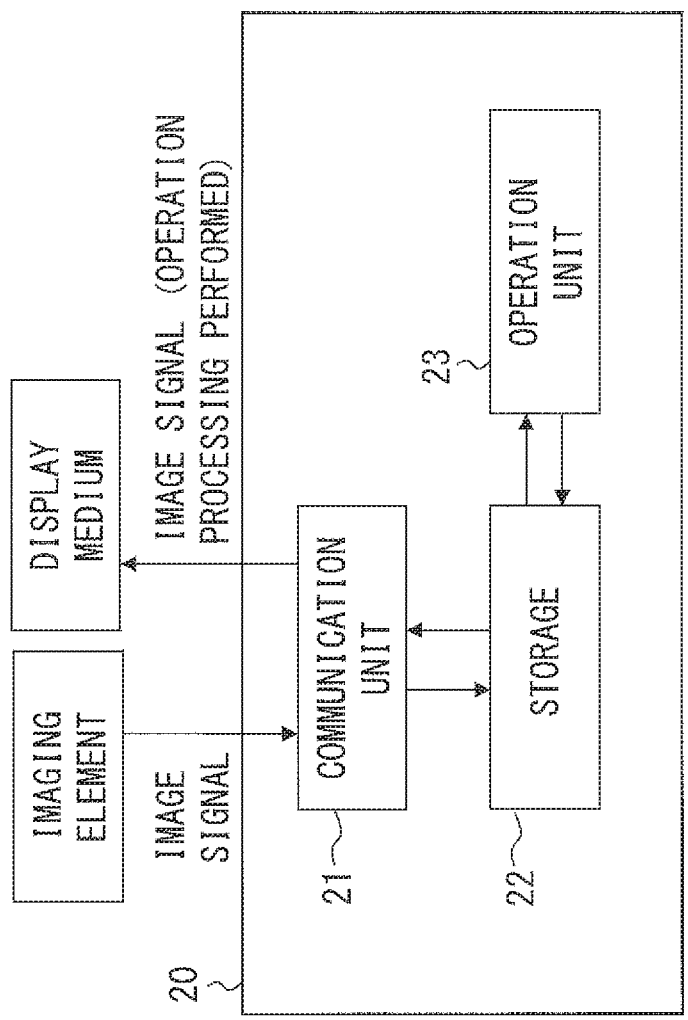
FIG. 2 illustrates a functional configuration of the operation device according to the first embodiment.

If a feature amount is estimated for each colony as disclosed in Japanese Laid-open Patent Publication No. 2011-229409, it will not be possible to estimate a mutation of an iPS cell that occurs in a colony. Thus, a conventional technology is not sufficient to determine a quality of an iPS cell. Thus, a technology has been desired that makes it possible to determine a quality of an iPS cell successfully, and an object of the present invention is to provide such a technology.

In order to solve the problems above, an indicator is generated that determines a quality of an iPS cell more specifically by applying the technology that is disclosed in Japanese Laid-open Patent Publication No. 2014-209085 and obtains a precise phase distribution of a phase object, such as a cell, that has a three-dimensional structure.

A configuration of a microscope 1 and an operation device 20 that implement a method for assisting in evaluating a pluripotent stem cell (hereinafter also referred to as an iPS cell) without stains according to a first embodiment of the present invention will now be described with reference to the drawings. FIG. 1 illustrates the configuration of the microscope 1 and the operation device 20.

The microscope 1 is a differential interference contrast microscope that forms an optical image in which a structure of a phase object such as a biological cell is represented as an image intensity distribution. The microscope 1 includes an illumination optical system 2, a stage (not illustrated) on which a sample S is fixed, an imaging optical system 3, and an imaging element 15. Further, the microscope 1 is connected to the operation device 20.

The sample S is a biological sample that includes, for example, a colony including a biological cell such as an iPS cell, and a culture solution, and is a phase object through which light is transmitted and that causes a phase difference in the transmitted light. The stage (not illustrated) on which the sample S is fixed is controlled to be movable in an optical direction of the optical systems and in a plane perpendicular to the optical direction of the optical systems.

The illumination optical system 2 includes a light source 4, a collector lens 5, a mirror 7, a polarizing plate 8, a quarter wave plate 16, a differential interference contrast microscope (DIC) prism 9, and a condenser lens 6. The imaging optical system 3 includes an objective 10, a DIC prism 12, a polarizing plate 13, a mirror 11, and a tube lens 14. The imaging element 15 is, for example, a CCD camera, and converts light into an image signal. The DIC prisms 9 and 12 are respectively arranged at a pupil position or a pupil-conjugate position of the condenser lens 6 and at a pupil position or a pupil-conjugate position of the objective 10.

In the illumination optical system 2, the polarizing plate 8 converts incident light into polarized light having a single vibration plane. The DIC prism 9 is also called a Nomarski prism, and splits light that enters through the polarizing plate 8 into two pieces of polarized light each having a vibration plane, the respective vibration planes being perpendicular to each other. The two pieces of polarized light respectively enter positions in the sample S that are each shifted by a shift amount (hereinafter also referred to as a shear amount), the respective shift amounts being slightly different from each other. Thus, the two pieces of polarized light respectively pass through the sample S at positions of different thicknesses and different refractive indexes, and images of the two pieces of polarized light are respectively formed in the imaging optical system 3 via different optical path lengths, so a phase difference occurs between the two pieces of polarized light. The phase difference is also referred to as a retardation. Further, a direction in which each of the two pieces of polarized light is shifted is also referred to as a shear direction.

In the imaging optical system 3, the DIC prism 12 combines the incident two pieces of polarized light into light having a single vibration plane. A light interference occurs in this process, and a differential image in which a contrast is formed on the basis of a phase difference between the two pieces of polarized light is formed on the imaging element 15. In other words, the microscope 1 is a microscope that is able to create an image of a structure of the sample S by converting a phase distribution into an image intensity distribution.

Further, the DIC prisms 9 and 12 are each controlled to rotate so as to be controlled to change a shear direction. Further, the polarizing plate 8 is also controlled to rotate so as to change a retardation. More particularly, the polarizing plate 8 changes a retardation so as to be controlled to change a contrast of an image that is formed on the imaging element 15. In other words, the microscope 1 is a microscope that is able to change a shear direction and that functions to obtain a plurality of images of different image contrasts, as in the case of the configuration of the microscopic system 100 disclosed in Japanese Laid-open Patent Publication No. 2014-209085. For example, the above-described controls performed on the DIC prisms 9 and 12 and the polarizing plate 8 may be performed in conjunction with each other by a computer connected to the microscope 1.

The operation device 20 is connected to the imaging element 15 and is a computer that has a function that performs operation processing on a signal of an image captured by the imaging element 15. Further, the operation device 20 is connected to an image display medium such as a monitor (not illustrated), and outputs, to the image display medium, an image signal on which operation processing has been performed so as to display an image. The computer that performs the above-described controls on the DIC prisms 9 and 12 and the polarizing plate 8 and the operation device 20 may be one computer. In other words, one computer may have a function of the operation device 20 and may perform the above-described controls on the DIC prisms 9 and 12 and the polarizing plate 8.

FIG. 2 illustrates a functional configuration of the operation device 20. The operation device 20 includes a communication unit 21, a storage 22, and an operation unit 23 in its functional configuration.

The communication unit 21 receives a signal of an image captured by the imaging element 15 and outputs, to the image display medium, data of, for example, an image signal on which operation processing has been performed by the operation device 20.

The storage 22 transmits an image signal received by the communication unit 21 to the operation unit 23, and transmits an image signal received from the operation unit 23 to the communication unit 21. Further, the storage 22 functions as a storage device that stores an image signal temporarily.

The operation unit 23 performs operation processing using an image signal received from the storage 22. There are primarily three types of operation processing performed by the operation unit 23. The first one is processing of calculating, from a plurality of image signals of the sample S, a first phase distribution that is a phase distribution of the sample S. The second one is processing of extracting, from the first phase distribution, a region having a phase amount that is not less than a specified phase amount. The third one is processing of generating evaluation information that is an indicator used when a user evaluates a state of the sample S, using the region having a phase amount that is not less than the specified phase amount.

The specified phase amount is a phase amount that is included in a somatic cell when an iPS cell has been mutated into the somatic cell. In other words, the region having a phase amount that is not less than a specified phase amount is similar to a region in which there exist no iPS cells, which are pluripotent, due to, for example, a mutation of the iPS cell. In the present embodiment, a phase amount of a mitochondrion in a somatic cell is used as a specified phase amount. The reason is that this may be a determination reference to determine whether there exists a mutation of an iPS cell because a mitochondrial metabolism is different in an iPS cell than in other somatic cells into which the iPS cell may be mutated, which results in changing a phase amount included in a cell.

In a general somatic cell, a TCA cycle that is a process in which energy is generated in a mitochondrion is performed actively. On the other hand, it is known that, in an iPS cell, the activity of a mitochondrion is not active and the mitochondrial morphology and the number of mitochondria are different from the case of a somatic cell. Thus, due to differences in the mitochondrial morphology and in the number of mitochondria, a difference in phase amount occurs between an iPS cell and other somatic cells into which an iPS cell may be mutated.

In the present invention, a region having a phase amount that is not less than a specified phase amount (a phase amount of a mitochondrion in a somatic cell) is calculated, and evaluation information is generated from the region having a phase amount that is not less than the specified phase amount, the evaluation information being used to evaluate a state of a biological sample based on an intracellular distribution amount of a mitochondrion in a somatic cell. This permits a user to determine whether there exists a mutation of an iPS cell. A specific method for evaluating an iPS cell will be described later.

Figure 3:
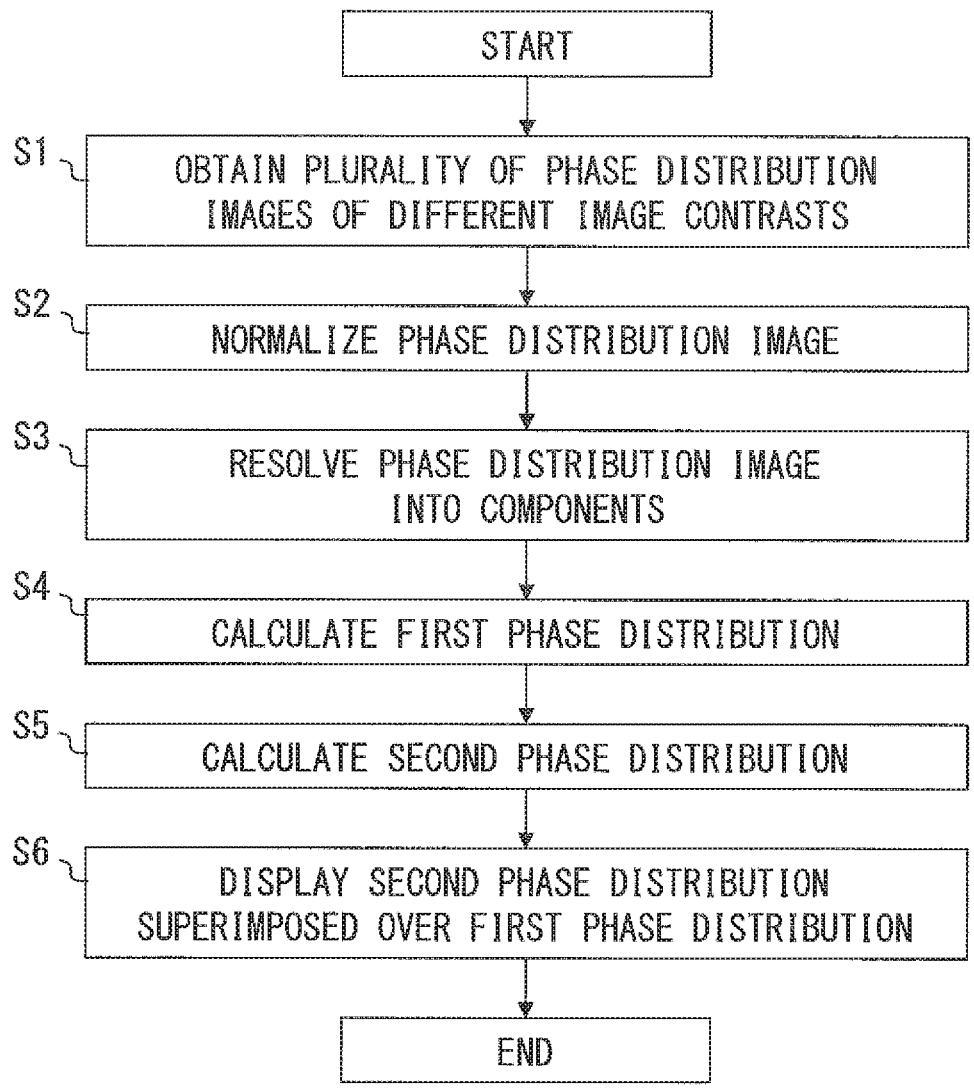
FIG. 3 is a flowchart of a method for assisting an evaluation without stains according to the first embodiment.

Using the microscope 1 and the operation device 20 that have the configuration described above, a method for assisting an evaluation without stains is implemented, the method providing a user with information (evaluation information) that is an indicator to determine a quality of an iPS cell included in the sample S. Specifically, the evaluation assisting method is a method that assists a user in determining a quality of an iPS cell by providing the evaluation information used to identify a mutation of an iPS cell. FIG. 3 is a flowchart that illustrates a procedure of the method for assisting in evaluating an iPS cell without stains according to the present embodiment. The method for assisting in evaluating an iPS cell without stains is described below with reference to FIG. 3. The processing of calculating a first phase distribution in Step S1 to Step S4 can be performed using a technology disclosed in Japanese Laid-open Patent Publication No. 2014-209085.

In Step S1, a plurality of phase distribution images of the sample S that have different image contrasts are obtained by the microscope 1. Specifically, two phase distribution images are obtained in a specified shear direction by the polarizing plate 8 being controlled such that a retardation is ±θ. Further, two phase distribution images are obtained in a state in which the shear direction is changed by the DIC prisms 9 and 12, by the polarizing plate 8 being controlled in the same way. In other words, in Step S1, two phase distribution images of different image contrasts are obtained by the microscope 1 for each shear direction. All of the obtained phase distribution images are transmitted to the operation device 20, and transmitted to the operation unit 23 through the communication unit 21 and the storage 22.

In Step S2, the operation unit 23 creates a difference-operation image and a sum-operation image from the phase distribution images obtained in Step S1, and divides the difference-operation image by the sum-operation image so as to calculate a normalized phase distribution image. The difference-operation image is an image obtained by performing a difference operation on an image whose retardation is symmetric (±θ), and is an image component that corresponds to a phase distribution of an iPS cell. The sum-operation image is an image obtained by performing a sum operation on an image whose retardation is symmetric (±θ), and is an image component that indicates, for example, an illumination distribution when an iPS cell is observed. Thus, the difference-operation image is normalized by dividing the difference-operation image by the sum-operation image, which results in being able to extract only an image component in which a phase distribution of the sample S and an optical response property (also referred to as an optical transfer function: OTF) are convolved. The operation unit 23 calculates a normalized phase distribution image for each shear direction, so two normalized phase distribution images are obtained here.

In Step S3, the normalized phase distribution image is resolved into three spatial frequency components by the operation unit 23 performing operational processing on the phase distribution image using a plurality of kernels of different sizes. The spatial frequency component obtained by resolving the phase distribution image is constituted of a background component whose spatial frequency is lowest, a refractive component formed by light refracted in the sample S, and a structure component whose special frequency is highest and that is formed by light diffracted with a structure within the sample S. First, averaging processing is performed multiple times using an averaging filter with a large kernel size (for example, a kernel size of 100×100), so as to calculate a background component of a phase distribution image. Next, with respect to an image from which a disturbance such as the non-uniformity in the field of view has been removed by subtracting the background component from the normalized phase distribution image, averaging processing is performed multiple times using an averaging filter with a small kernel size (for example, a kernel size of 20×20), so as to calculate a refractive component of the phase distribution image. Then, the background component and the refractive component are subtracted from the normalized phase distribution image, so as to calculate a structure component of the phase distribution image. The operation unit 23 resolves two normalized phase distribution images in different shear directions that are obtained in Step S2, so as to calculate the background component, the refractive component, and the structure component.

In Step S4, with respect to the structure component obtained in Step S3, deconvolution processing is performed using a corresponding OTF, so as to calculate a phase distribution of the structure component. The operation unit 23 calculates, for each shear direction, a phase distribution of the structure component from which a disturbance such as the non-uniformity in the field of view (such as the background component and the refractive component) has been removed. Finally, the phase distributions of the structure component that are calculated in the respective shear directions are combined so as to calculate a first phase distribution of the sample S from which effects of the shear directions have been removed. The first phase distribution calculated by performing the operation processing in Steps S1 to S4 is a phase distribution of structure components situated near a focal point. An image of the first phase distribution generated from the first phase distribution may be output to the image display medium by the communication unit 21 at this point.

Figure 4:
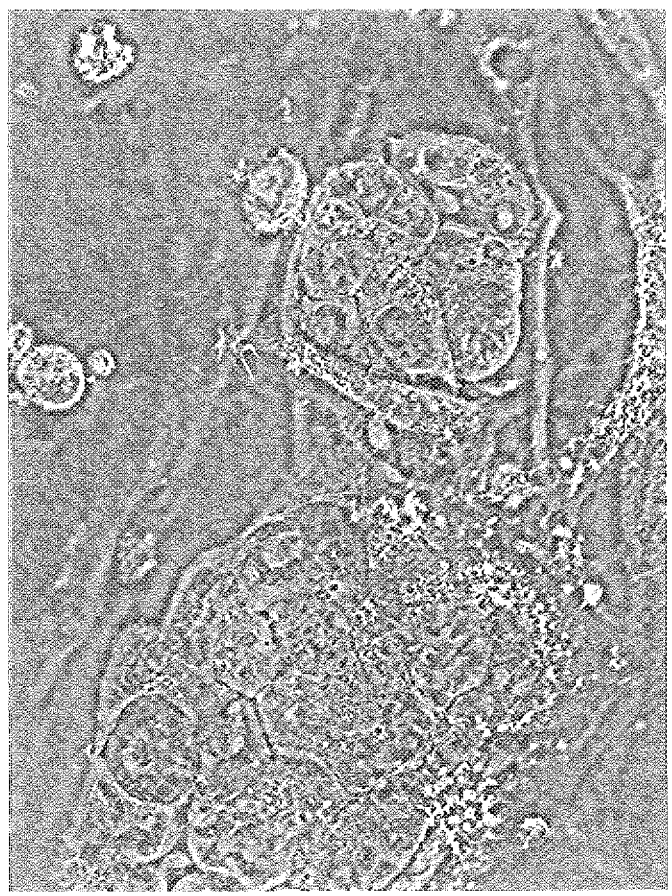
FIG. 4 illustrates an example of an image of a first phase distribution.

FIG. 4 illustrates an example of an image of the first phase distribution that is output to the image display medium. It is known that a mitochondrion has a fine structure, so in the following steps, a phase amount that corresponds to a mitochondrion is extracted from the phase distribution of a structure component (the first phase distribution) that is calculated in Steps S1 to S4.

In Step S5, the operation unit 23 extracts, from the first phase distribution, a region having a phase amount that is not less than a specified phase amount. As described above, the specified phase amount is a phase amount of a mitochondrion in a somatic cell. Here, the region having a phase amount that is not less than a specified phase amount refers to a region in which there exist no iPS cells, which are pluripotent.

In Step S5, for example, a phase amount of a sample of a somatic cell is measured in advance using the microscope 1 and the operation device 20, a value of a phase amount corresponding to a mitochondrion in the somatic cell is calculated, and a region having a phase amount that is not less than a specified phase amount can be extracted in the phase distribution of a structure component using the value as a threshold, the specified phase amount being not less than the threshold.

When a range from which a region having a phase amount that is not less than a specified phase amount is extracted is a measurement range, the measurement range can be changed by performing a setting. For example, the measurement range may be determined by a user visually confirming the image of the first phase distribution (such as the image illustrated in FIG. 4) which is output in Step S4 to specify a region in the image. The measurement range may be an outline of an aggregation formed by cells or may be any range within the outline. Specifically, if the image area of one cell is set to be the measurement range, it will be possible to perform an evaluation for each cell.

The measurement range from which a region having a phase amount that is not less than a specified phase amount is extracted is not limited to a range discretionarily determined by a user, but a range in which there exists a biological cell may be obtained from a first phase distribution and the obtained range may be set to be the measurement range. For example, there is no change in phase distribution in a range in which there exist no biological cells, which results in a low image contrast. Thus, it is possible to extract a range in which an image contrast is low and there exist no biological cells by performing convolution processing on a normalized phase distribution image using a matrix operator that performs differentiation in a shear direction. In other words, it is possible to extract a range in which there exists a biological cell and to set the extracted range to be the measurement range.

Figure 5:
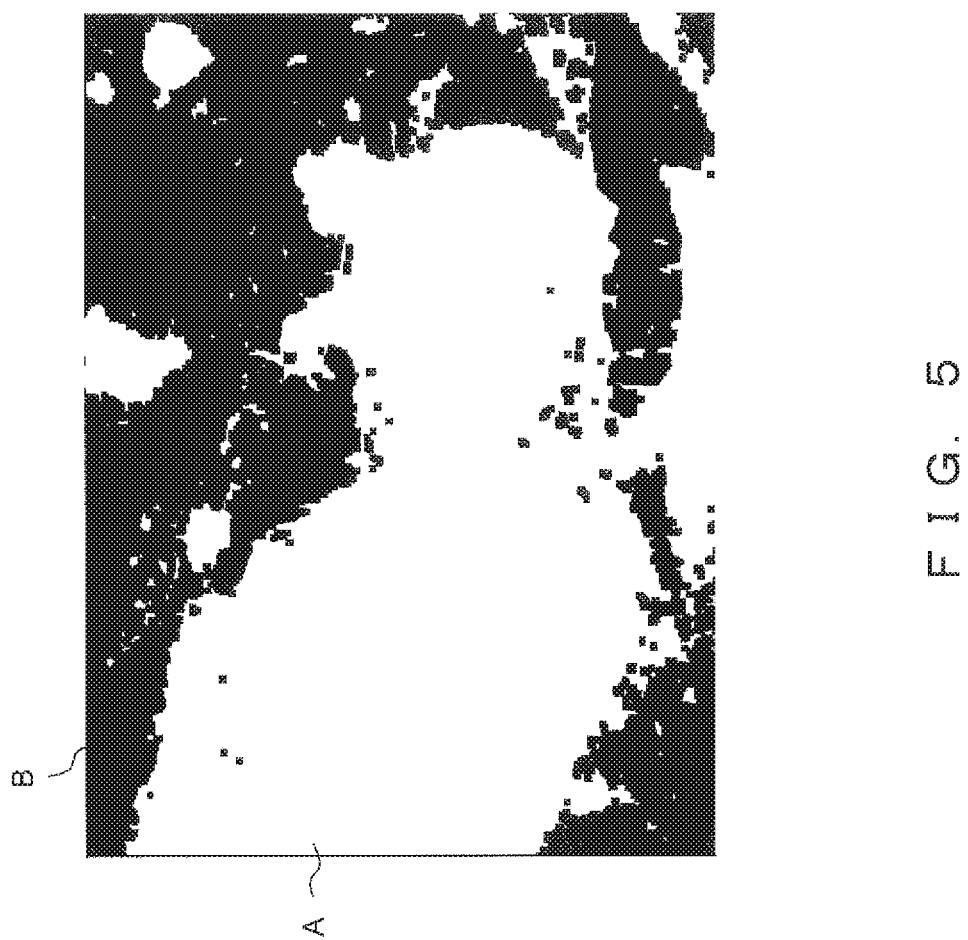
FIG. 5 illustrates the image of the first phase distribution illustrated in FIG. 4 which is binarized between a region in which there exists a biological cell and a region in which there exist no biological cells.

FIG. 5 illustrates an image that indicates a measurement range in the first phase distribution illustrated in FIG. 4 when a range in which there exists a biological cell is set to be the measurement range, wherein the image is binarized, in which the measurement range (pixel) is one and the other portion (pixel) is zero. In FIG. 5, a region A indicates a measurement range, and a range B indicates the other region.

Figure 6:
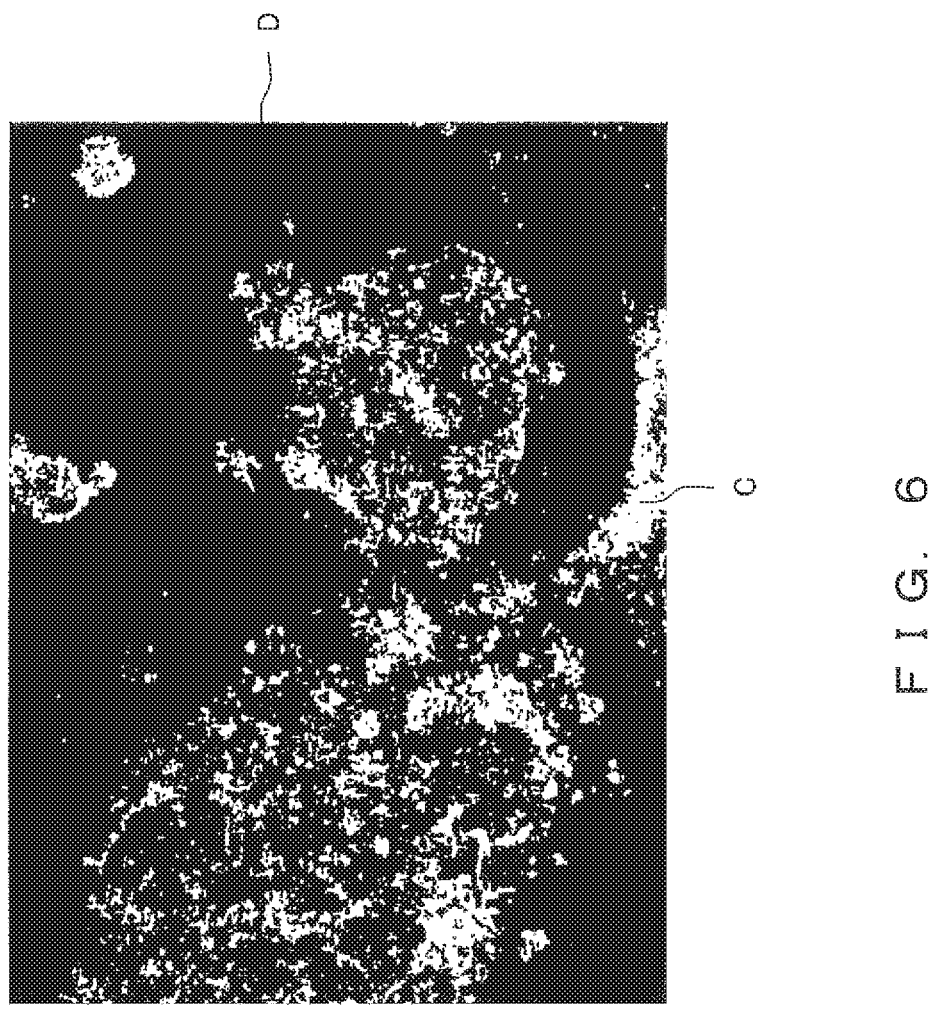
FIG. 6 illustrates the binarized image in FIG. 5 between a region having a phase amount that is not less than a specified phase amount and a region not having the phase amount that is not less than the specified phase amount.

FIG. 6 illustrates an image that indicates a region in the measurement range of FIG. 5 that has a phase amount that is not less than a specified phase amount and that is calculated in Step S5, wherein the image is binarized, in which the range having a phase amount that is not less than the specified phase amount (pixel) is one and the other portion (pixel) is zero. In FIG. 6, a region C indicates a region having a phase amount that is not less than a specified phase amount, and a region D indicates the other region. The processing of setting a measurement range and extracting a region having a phase amount that is not less than a specified phase amount in Step S5 is internally performed in the operation device 20. Thus, actually, there is no need to output images illustrated in FIGS. 5 and 6 to the image display medium, but corresponding images have been illustrated for convenience of description.

Figure 7:
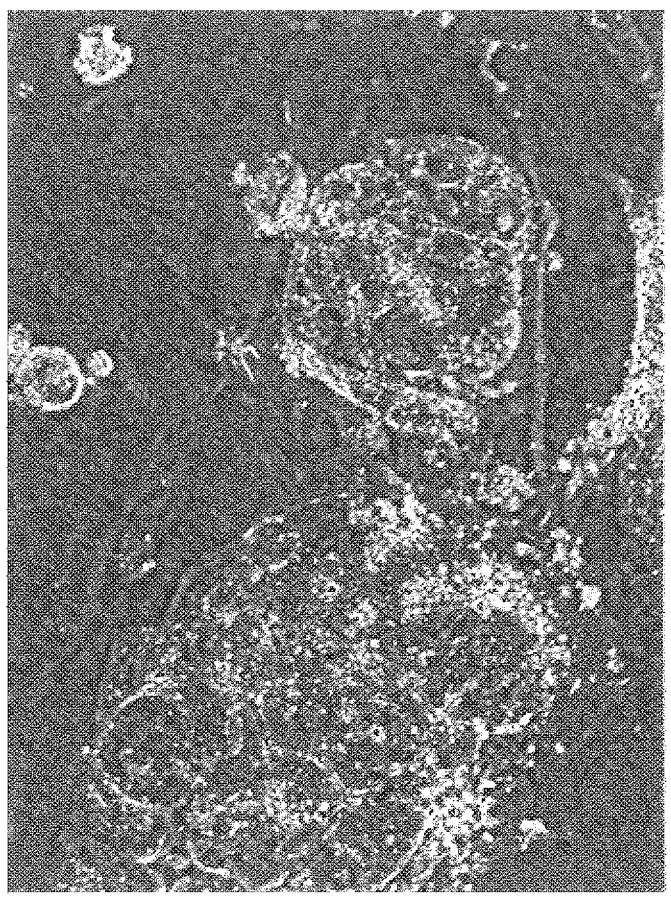
FIG. 7 illustrates an image obtained by superimposing the image of FIG. 6 over the image of FIG. 4.

In Step S6, the operation unit 23 generates an image in which a region having a phase amount that is not less than a specified phase amount is distinguished from the other region in an image generated from the first phase distribution. For example, an image signal is generated in which a region having a phase amount that is not less than a specified phase amount is superimposed over the image of the first phase distribution, and the image signal is output to the image display medium through the communication unit 21. FIG. 7 illustrates an image obtained when the region of FIG. 6 that has a phase amount that is not less than a specified phase amount is superimposed with a specified color over the image of the first phase distribution illustrated in FIG. 4 and is output to the image display medium. When the processing described above is completed, the flowchart is terminated.

Using the image displayed on the image display medium by performing the process of Step S6, it is possible to easily identify a portion in which an iPS cell has been mutated because a portion in which the pluripotency is low due to the mutation of the iPS cell is distinguished with a specified color. In other words, it is possible to easily identify a region in which an iPS cell remains pluripotent. The process of Step S6 is generating an image (evaluation information) that is an indicator used when a user evaluates a state of the sample S using an image of the first phase distribution and a region having a phase amount that is not less than a specified phase amount, and presenting the generated image to the user.

The above-described method for assisting an evaluation without stains according to the present embodiment makes it possible to provide evaluation information that is an indicator to determine a quality of an iPS cell successfully. According to the present embodiment, it is possible to easily identify, within a colony, a portion in which there exists a cell that has lost the pluripotency from an image in which a region having a phase amount that is not less than a specified phase amount is superimposed over an image of a first phase distribution.

Further, when a range in which there exists a biological cell is set as a measurement range, a range that does not include a biological cell is automatically excluded, which results in being able to calculate a proportion of a mutation of an iPS cell more precisely than when the measurement range is discretionarily set by a user.

Figure 8:
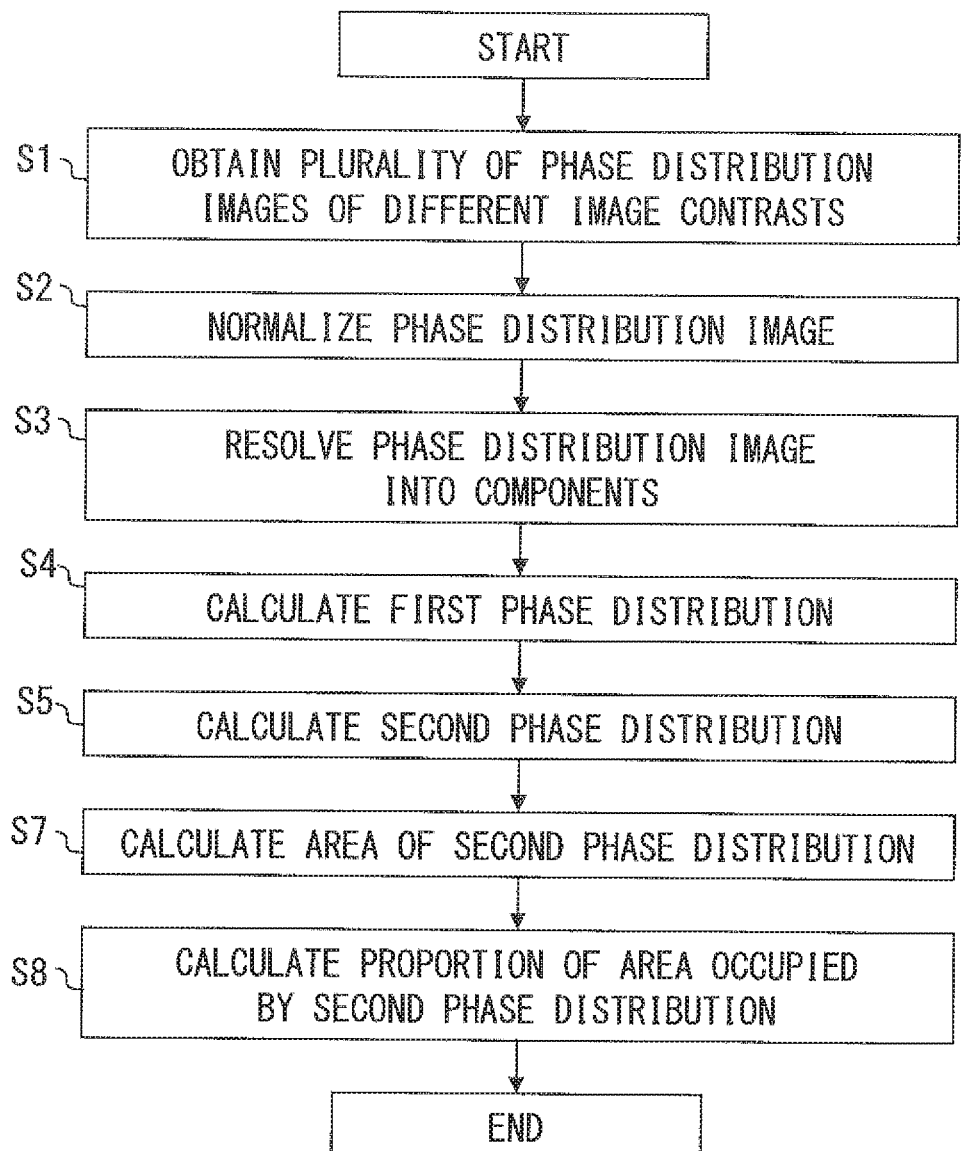
FIG. 8 is a flowchart of a variation of the method for assisting an evaluating without stains according to the first embodiment.

A variation of the method for assisting an evaluation without stains according to the first embodiment is described below. FIG. 8 is a flowchart that illustrates a procedure of the variation of the method for assisting in evaluating an iPS cell without stains. The descriptions of the processes of Steps S1 to S5 in FIG. 8 (calculating a first phase distribution and extracting a region having a phase amount that is not less than a specified phase amount) are omitted because they are similar to the processes of Steps S1 to S5 illustrated in FIG. 3.

In Step S7, the operation unit 23 calculates the area, in the measurement range of the image, occupied by the region having a phase amount that is not less than a specified phase amount. When the area is calculated, for example, a region in an image signal is binarized in which a portion (pixel) having a phase amount that is not less than a specified phase amount is one and the other portion (pixel) is zero, as illustrated in FIG. 6. The area occupied by the region having a phase amount that is not less than a specified phase amount can be calculated by calculating the area of a pixel to which one is assigned.

In Step S8, the operation unit 23 calculates a proportion of the area occupied in the measurement range by the region having a phase amount that is not less than a specified phase amount, and outputs the area proportion to the image display medium through the communication unit 21.

It is possible to know a proportion of a region in which an iPS cell has been mutated by referring to the area proportion displayed on the image display medium in Step S8. In other words, it is possible to know a proportion of a region in which an iPS cell remains pluripotent in the measurement range, and to determine a quality of an iPS cell included in the sample S on the basis of the size of the proportion. The process of Step S8 is generating an area proportion (evaluation information) that is an indicator used when a user evaluates a state of the sample S using a region having a phase amount that is not less than a specified phase amount, and presenting the generated area proportion to the user.

The above-described variation of the method for assisting an evaluation without stains also makes it possible to provide evaluation information that is an indicator to determine a quality of an iPS cell successfully. In particular, according to this variation, it is possible to represent a proportion of a mutation of an iPS cell in a measurement range as a specific value by calculating a ratio of the area of a region in which an iPS cell has been mutated and the area of the measurement range, which permits a user to determine a quality of an iPS cell on the basis of a more objective indicator. Further, it is also possible to approximately obtain the proportion for each cell by obtaining a proportion of a region for each unit area, the region being a region, in a measurement range, in which an iPS cell has been mutated.

Further, the method for assigning an evaluation without stains may be implemented by combining the first embodiment and the variation described above, the method being used to determine a quality of an iPS cell. For example, the operation device 20 generates an image in which a region having a phase amount that is not less than a specified phase amount is superimposed over an image of a first phase distribution and displays the generated image on the image display medium. Further, a user may specify a specific region (such as a specific colony or cell) from the displayed image, and the operation device 20 may calculate a proportion of the area occupied in the specific region by the region having a phase amount that is not less than a specified phase amount and may display the area proportion on the image display medium. This method permits a user to determine a location in which there exists a cell that has lost the pluripotency, on the basis of the image in which the region having a phase amount that is not less than a specified phase amount is superimposed over the first phase distribution. This results in being able to determine a quality of an iPS cell more objectively by obtaining an area proportion of the region having a phase amount that is not less than a specified phase amount, in a specific cell or colony, wherein the specific cell or colony is to be evaluated more objectively from the image.

Figure 9:
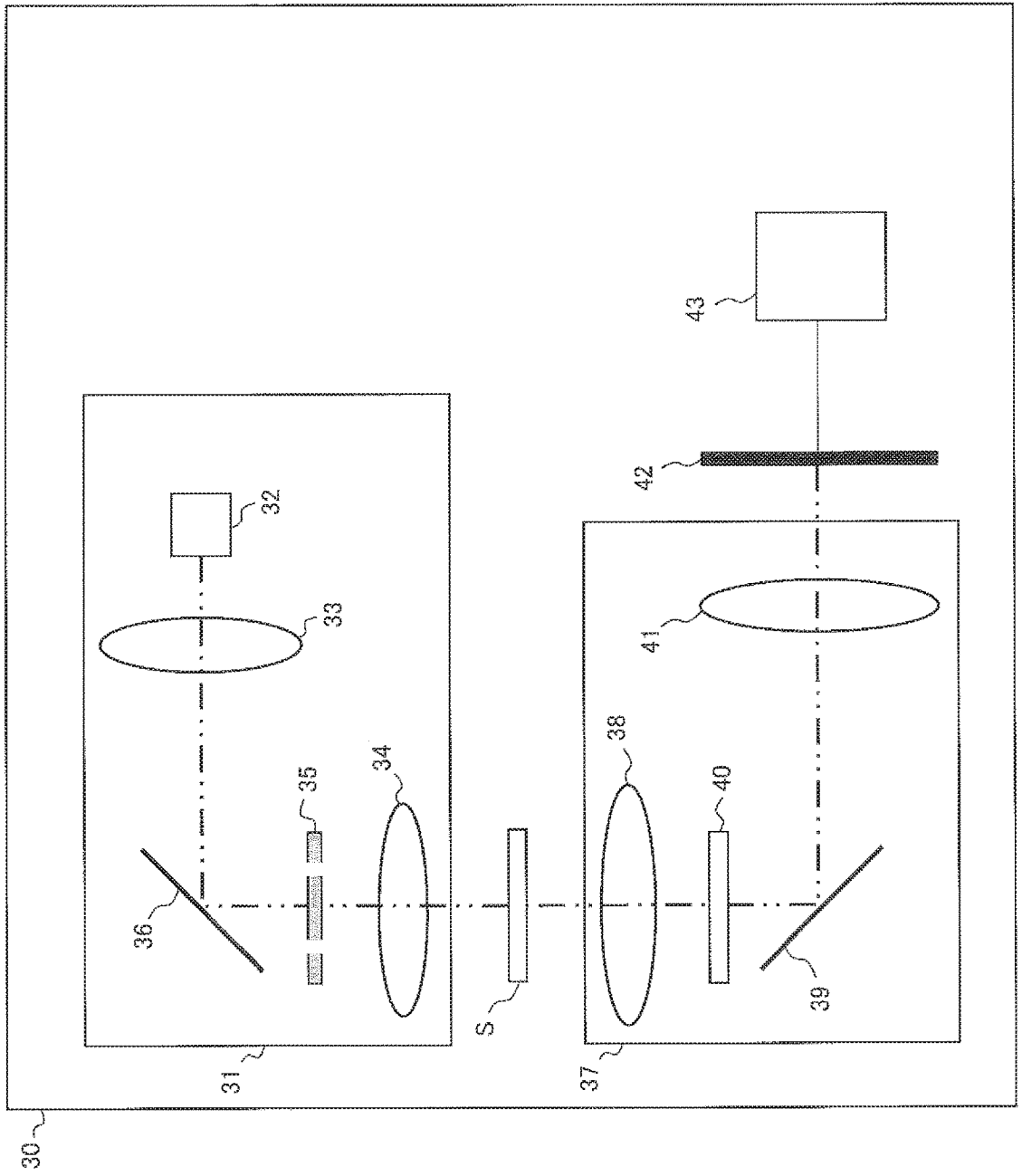
FIG. 9 illustrates a configuration of a microscope and an operation device according to a second embodiment.

A configuration of a microscope 30 and an operation device 43 that implement a method for assisting in evaluating an iPS cell without stains according to a second embodiment of the present invention will now be described with reference to FIG. 9. FIG. 9 illustrates the configuration of the microscope 30 and the operation device 43.

The microscope 30 is a phase contrast microscope that forms an optical image in which a structure of a phase object such as a biological cell is represented as an image intensity distribution. The microscope 30 includes an illumination optical system 31, a stage (not illustrated) on which the sample S is fixed, an imaging optical system 37, and an imaging element 42. Further, the microscope 30 is connected to the operation device 43. As in the case of the sample S described in the first embodiment, the sample S is a biological sample that includes, for example, a colony including a biological cell such as an iPS cell, and a culture solution.

As the illumination optical system 31, the microscope 30 includes a light source 32, a collector lens 33, a mirror 36, a ring slit 35, and a condenser lens 34. As the imaging optical system 37, the microscope 30 further includes an objective 38, a liquid crystal element 40, a mirror 39, and a tube lens 41. The imaging element 42 is, for example, a CCD camera, and converts light into an image signal.

The liquid crystal element 40 is arranged at a position conjugate with the ring slit 35, and in the microscope 30, a phase amount of the liquid crystal element 40 is changed so as to change a contrast of an image to be formed.

The operation device 43 has a functional configuration similar to that of the operation device 20, wherein the operation device 43 calculates a first phase distribution from signals of images of the sample S and extracts a region having a phase amount that is not less than a specified phase amount, the images being captured by the microscope 30.

Thus, according to the microscope 30 that is a phase contrast microscope, it is also possible to capture two images of different image contrasts when the phase amount of the liquid crystal element 40 is changed by $\pm\psi$, to calculate a difference-operation image and a sum-operation image from these images, and to calculate a normalized phase distribution image, as in the case of the microscope 1. The processes described above correspond to the processes up to Step S2 in FIG. 3. After that, in a procedure similar to that of the first embodiment, it is possible to implement the method for assisting in evaluating an iPS cell without stains using the operation device 43. In the microscope 30 of the present embodiment, images obtained by changing an image contrast using two pieces of polarized light respectively radiated onto different positions of the sample S are not calculated, so the method for assisting an evaluation without stains according to the present embodiment is different from the method for assisting an evaluation without stains according to the first embodiment in that it does not include removing effects of shear directions.

The above-described method for assisting an evaluation without stains according to the present embodiment also makes it possible to provide evaluation information that is an indicator to determine a quality of an iPS cell successfully.

Figure 10:
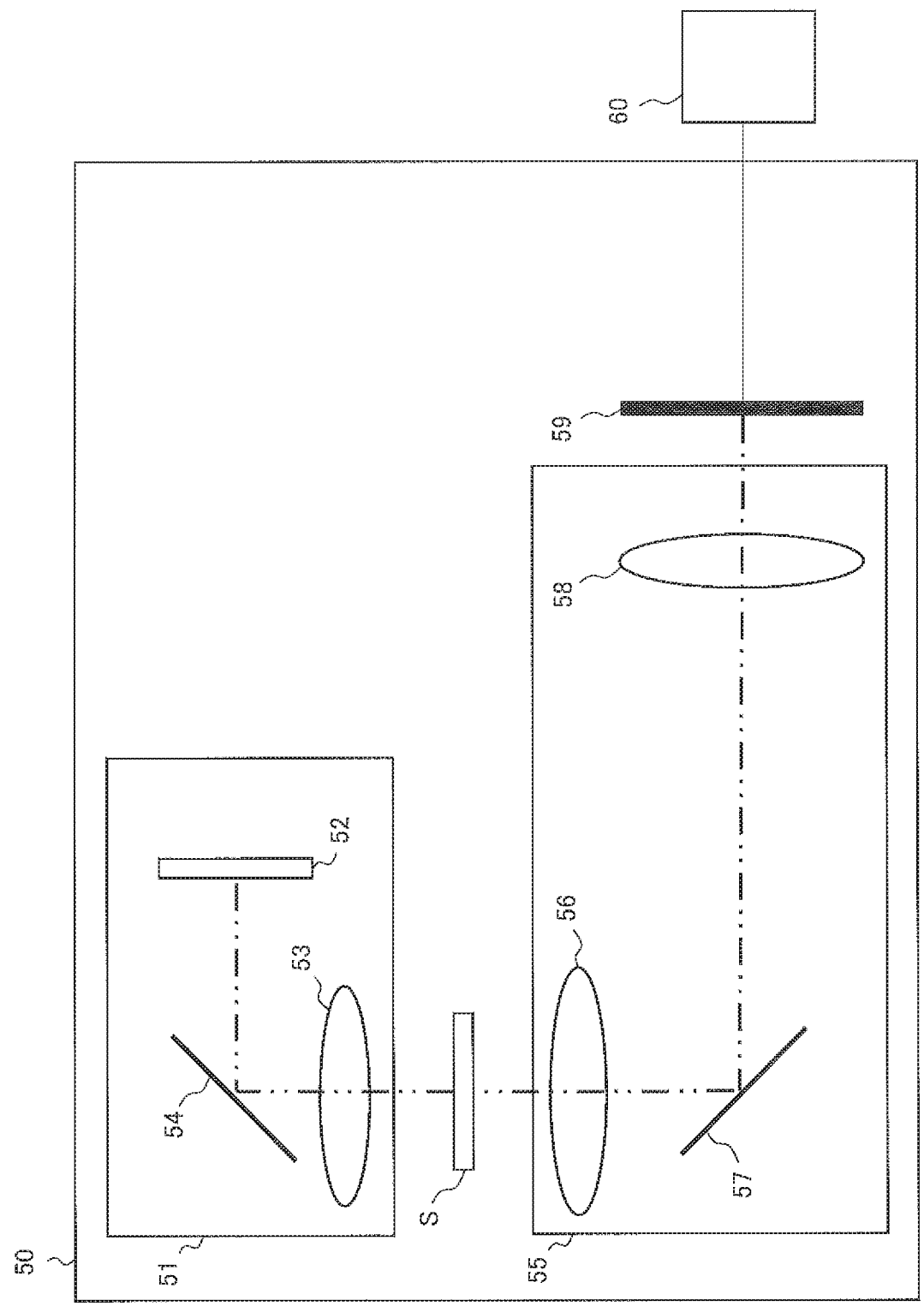
FIG. 10 illustrates a configuration of a microscope and an operation device according to a third embodiment.

A configuration of a microscope 50 and an operation device 60 that implement a method for assisting in evaluating an iPS cell without stains according to a third embodiment of the present invention will now be described with reference to FIG. 10. FIG. 10 illustrates the configuration of the microscope 50 and the operation device 60.

The microscope 50 is an oblique illumination microscope that forms an optical image in which a structure of a phase object such as a biological cell is represented as an image intensity distribution. The microscope 50 includes an illumination optical system 51, a stage (not illustrated) on which the sample S is fixed, an imaging optical system 55, and an imaging element 59. Further, the microscope 50 is connected to the operation device 60. As in the case of the sample S described in the first embodiment, the sample S is a biological sample that includes, for example, a colony including a biological cell such as an iPS cell, and a culture solution.

As the illumination optical system 51, the microscope 50 includes an LED 52 that is a light source, a condenser lens 53, and a mirror 54. As the imaging optical system 55, the microscope 50 further includes an objective 56, a mirror 57, and a tube lens 58. The imaging element 59 is, for example, a CCD camera, and converts light into an image signal.

Figure 11:
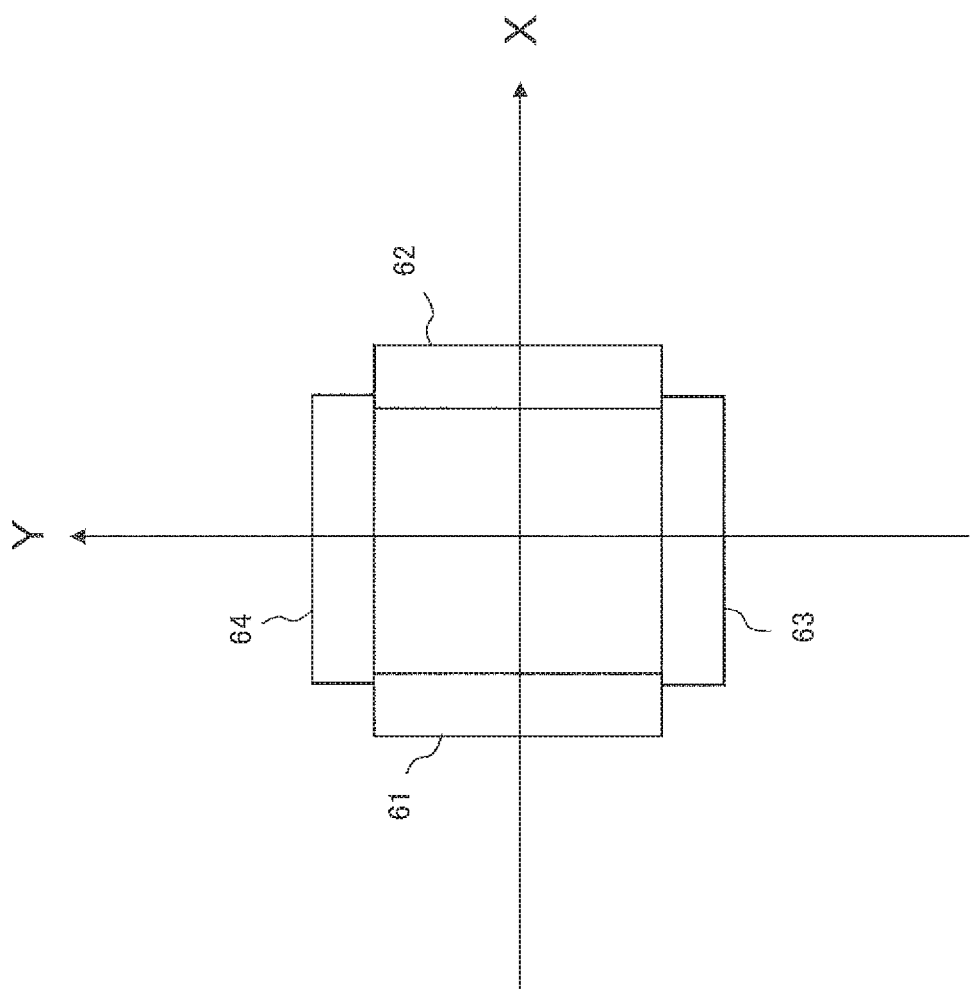
FIG. 11 illustrates an LED according to the third embodiment.

As illustrated in FIG. 11, the LED 52 is constituted of four LEDs 61, 62, 63, and 64 that are respectively arranged in four positions decentered from an optical axis of the illumination optical system 51, the four LEDs each controlling turning on/off of light. In other words, in the microscope 50, it is possible to perform an oblique illumination from four directions in a horizontal direction (an X direction) and in a vertical direction (a Y direction) illustrated in FIG. 11.

The operation device 60 has a functional configuration similar to that of the operation device 20, wherein the operation device 60 calculates a first phase distribution from signals of images of the sample and extracts a region having a phase amount that is not less than a specified phase amount, the images S being captured by the microscope 50.

Thus, according to the microscope 50 that is an oblique illumination microscope, it is also possible to calculate a first phase distribution, as in the case of the microscope 1. In the microscope 50, images are captured by oblique illumination performed by the horizontally arranged LEDs 61 and 62 (the LEDs 61 and 62 each illuminate the sample S at angles of ±ω, a difference-operation image and a sum-operation image are calculated from these images, and a normalized phase distribution image is calculated (corresponding to the processes up to Step S2 in FIG. 3). Likewise, a normalized phase distribution image is also calculated by oblique illumination performed by the vertically arranged LEDs 63 and 64. Then, as in the processes of Steps S3 and S4 in FIG. 3, a background component, a refractive component, and a structure component are extracted from the normalized phase distribution image, and a phase distribution of the structure component can be calculated. A first phase distribution can be obtained by vectorially combining phase distributions of a structure component that are respectively obtained from the vertical direction and the horizontal direction. After that, in a procedure similar to that of the first embodiment, it is possible to implement the method for assisting in evaluating an iPS cell without stains using the operation device 60.

In the microscope 50 of the present embodiment, images obtained by changing an image contrast using two pieces of polarized light respectively radiated onto different positions of the sample S are not calculated, so the method for assisting an evaluation without stains according to the present embodiment is different from the method for assisting an evaluation without stains according to the first embodiment in that it does not include removing effects of shear directions.

The above-described method for assisting an evaluation without stains according to the present embodiment also makes it possible to provide evaluation information that is an indicator to determine a quality of an iPS cell successfully.

Figure 12:
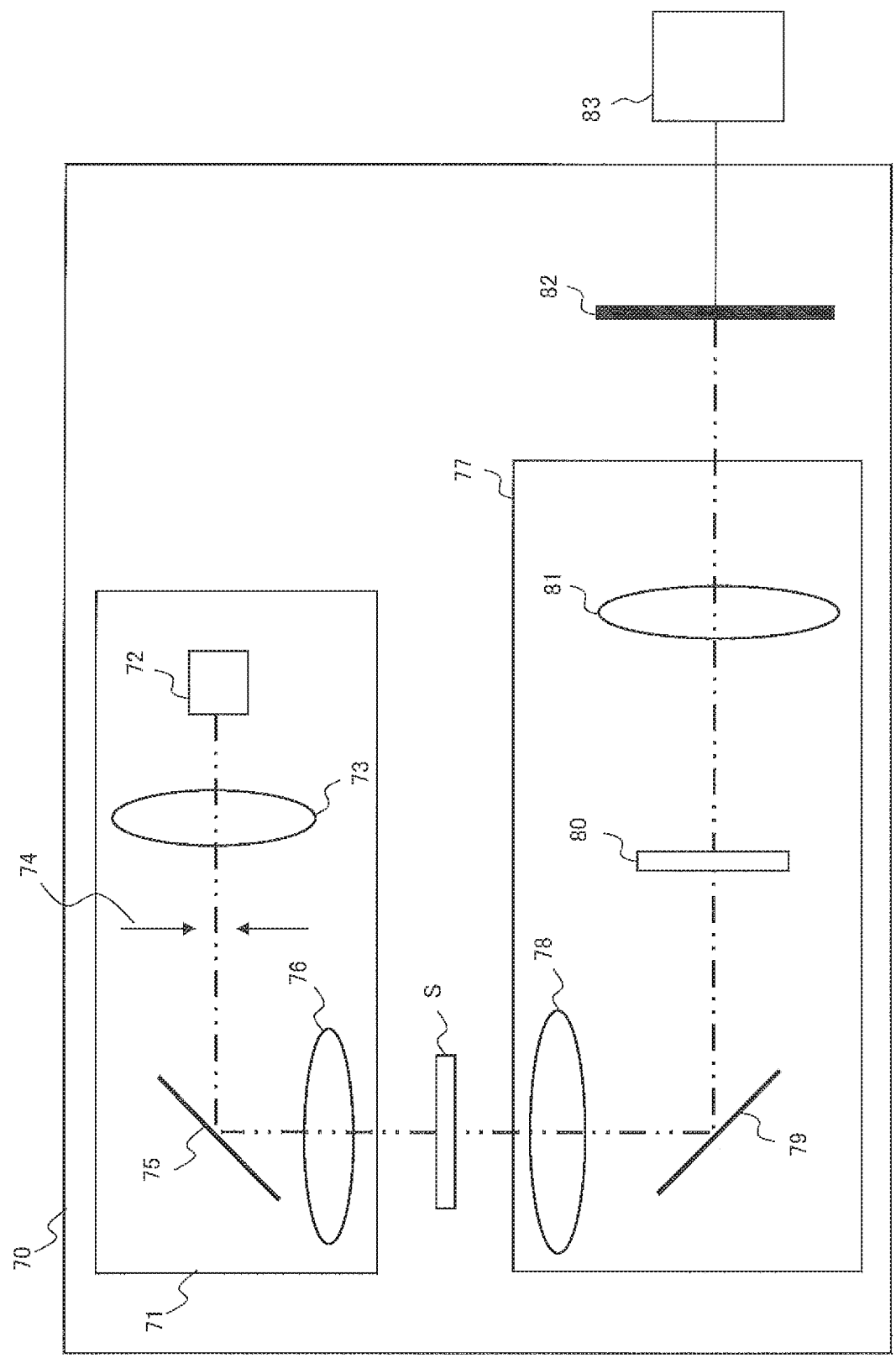
FIG. 12 illustrates a configuration of a microscope and an operation device according to a fourth embodiment.

A configuration of a microscope 70 and an operation device 83 that implement a method for assisting in evaluating an iPS cell without stains according to a fourth embodiment of the present invention will now be described with reference to FIG. 12. FIG. 12 illustrates the configuration of the microscope 70 and the operation device 83.

The microscope 70 is a decentered aperture microscope that forms an optical image in which a structure of a phase object such as a biological cell is represented as an image intensity distribution. The microscope 70 includes an illumination optical system 71, a stage (not illustrated) on which the sample S is fixed, an imaging optical system 77, and an imaging element 82 such as a CCD camera. Further, the microscope 70 is connected to the operation device 83. As in the case of the sample S described in the first embodiment, the sample S is a biological sample that includes, for example, a colony including a biological cell such as an iPS cell, and a culture solution.

As the illumination optical system 71, the microscope 70 includes a light source 72, a collector lens 73, a mirror 75, and a condenser lens 76. As the imaging optical system 77, the microscope 70 further includes an objective 78, a mirror 79, and a tube lens 81. The microscope 70 further includes an aperture stop 74 in the illumination optical system 71, and a light blocking device 80 at a pupil position of the objective 78 between the sample S and the imaging element 82.

The light blocking device 80 is a light blocking device that blocks light from the sample S, and has an aperture 80a that is a decentered aperture at a position decentered from an optical axis of the imaging optical system 77. The light blocking device 80 is controlled to rotate about the optical axis of the imaging optical system 77 so as to change a position of the aperture 80a in a plane perpendicular to the optical axis of the imaging optical system 77.

Figure 13:
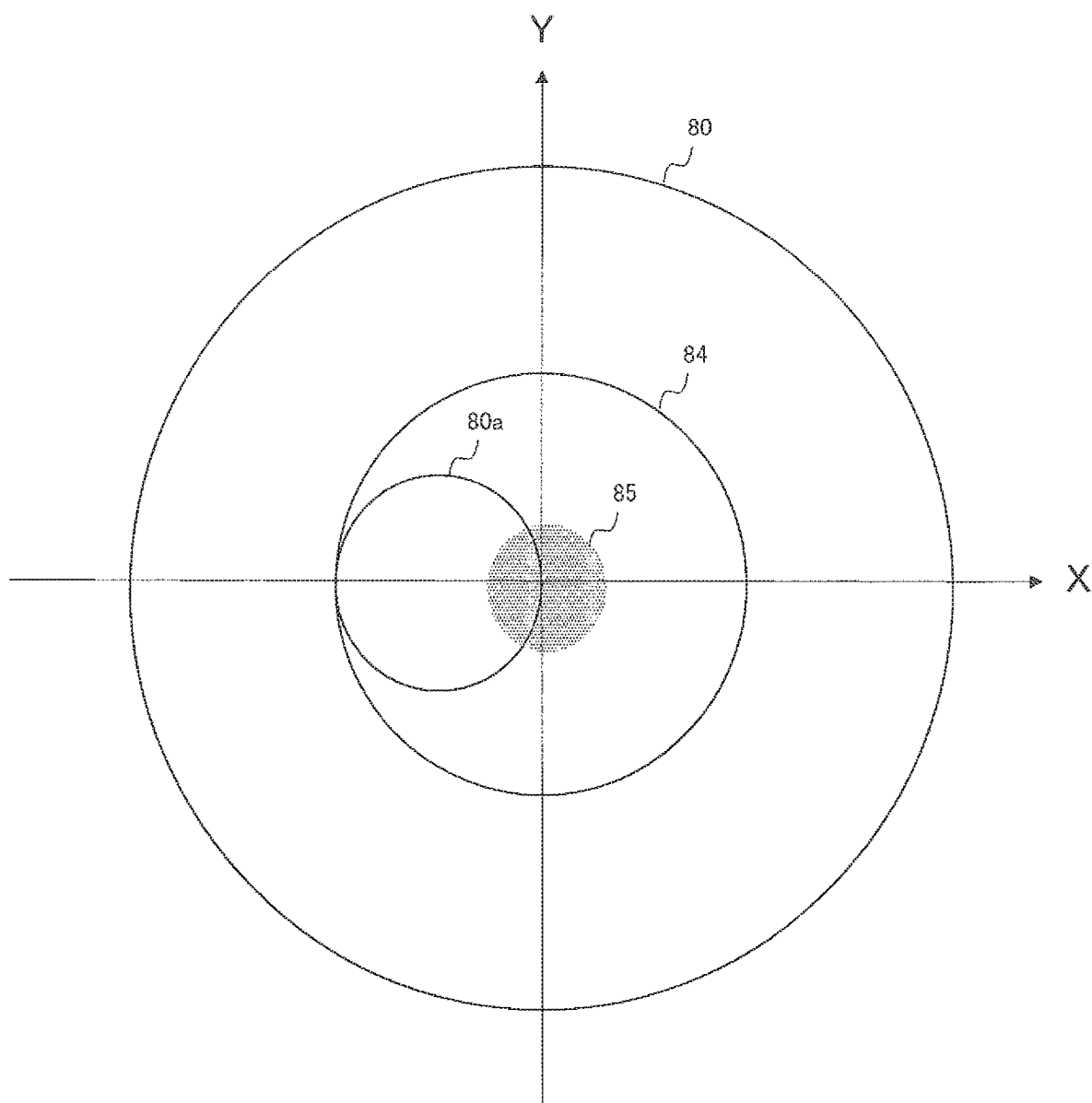
FIG. 13 illustrates a decentered aperture according to the fourth embodiment.

FIG. 13 illustrates a positional relationship between the light blocking device 80 and the aperture 80a. A region 85 marked by shading represents light that comes from the sample S illuminated by the illumination optical system 71 and is not diffracted by the sample S. The region represents a region in a pupil 84 of the objective 78 where the light reaches, when there does not exist the sample S that is a phase object or when the phase of the sample S is uniform. In other words, the aperture 80a in FIG. 13 is provided at a position in which the 0th-order light passes through a portion of the aperture 80a. Thus, 1st-order diffracted light in a specific direction that is diffracted by the sample S passes through the aperture 80a. Further, the aperture stop 74 of the illumination optical system 71 and the pupil 84 of the objective 78 are arranged at a position substantially optically conjugate with each other, and the region 85 represents a projection image of the aperture stop 74. Thus, it is possible to adjust a beam diameter in the pupil 84 of the objective 78 by reducing the aperture stop 74 up to a predetermined diameter, and in this case, the setting is performed such that the predetermined diameter does not fill the entirety of the pupil 84, as illustrated in FIG. 13.

In the configuration described above, even if illumination light is illuminated vertically on the sample S, 1st-order diffracted light in a specific direction that is diffracted by the sample S passes through the aperture 80a included in the light blocking device 80. Thus, as in the case of oblique illumination, it is possible to form, on the imaging element 82, an image in which a contrast of the sample S in a specific direction is brought out.

The operation device 83 has a functional configuration similar to that of the operation device 20, wherein the operation device 83 calculates a first phase distribution from signals of images of the sample S and extracts a region having a phase amount that is not less than a specified phase amount, the images being captured by the microscope 70.

As described above, even if the microscope 70 and the operation device 83 are used, it is possible to obtain images formed with pieces of 1st-order light in four directions, that is, two symmetric directions on an X axis in FIG. 13 and two symmetric directions on a Y axis in FIG. 13, by controlling the light blocking device 80 to rotate, so it is possible to calculate first and second phase distributions and to implement the method for assisting in evaluating an iPS cell without stains, in a procedure similar to that of the third embodiment.

The embodiments of the present invention make it possible to provide a method for assisting in evaluating a pluripotent stem cell without stains, a program, and an operation device, the method providing information that is an indicator to determine a quality of an iPS cell successfully.

The embodiments described above are just examples to facilitate understanding of the present invention, and the present invention is not limited to these embodiments. Various modifications and alterations may be made to the method for assigning an evaluation without stains, the operation device, and the program described above without departing from the spirit and scope of the invention specified in the claims. Further, the program described above may be stored in a non-transitory storage medium.

What is claimed is:

1. A method for assisting in evaluating a pluripotent stem cell without stains, the method comprising:
   forming a phase distribution image of the pluripotent stem cell from images of the pluripotent stem cell, the images of the pluripotent stem cell being captured using a microscope that converts a phase distribution into an image intensity distribution;
   setting, as a threshold, a phase amount of a mitochondrion in a somatic cell;
   extracting, from the phase distribution image, an image region having a phase amount that is not less than the threshold;
   generating first information distinguishing the phase distribution image from the image region;
   generating evaluation information indicating an extent to which the pluripotent stem cell remains pluripotent, the evaluation information being generated based on the first information; and
   displaying the evaluation information on an image display medium.

2. The method according to claim 1, wherein the evaluation information comprises an evaluation image in which the image region is superimposed over the phase distribution image.

3. The method according to claim 1, wherein the first information is an area of the image region.

4. The method according to claim 1, wherein a differential interference contrast microscope is used as the microscope.

5. The method according to claim 1, wherein a phase contrast microscope is used as the microscope.

6. The method according to claim 1, wherein an oblique illumination microscope is used as the microscope.

7. The method according to claim 1, wherein a decentered aperture microscope is used as the microscope.

8. The method according to claim 1, wherein the images of the pluripotent stem cell include, for each shear direction, two phase distribution images of different image contrasts obtained under different polarization states such that a retardation thereof is $\pm\theta$.

9. The method according to claim 1, wherein the generating the first information comprises generating an image in which the image region is superimposed over the phase distribution image.

10. The method according to claim 1, wherein the displaying the evaluation information on the image display medium includes superimposing, with a specified color, the image region over the phase distribution image and displaying a resultant image on the image display medium.

11. The method according to claim 1, further comprising:
    calculating an area within the phase distribution image occupied by the image region.

12. The method according to claim 11, further comprising:
    calculating a proportion of the area occupied by the image region within the phase distribution image.

13. The method according to claim 1, wherein the evaluation information is generated by calculating a proportion of an area of the pluripotent stem cell occupied by the image region.

14. A device comprising:
    a communication unit and
    a computer configured to:
      form a phase distribution image of a pluripotent stem cell from images of the pluripotent stem cell, the images of the pluripotent stem cell being captured using a microscope that converts a phase distribution into an image intensity distribution and being received from the microscope via the communication unit;
      set, as a threshold, a phase amount of a mitochondrion in a somatic cell;
      extract, from the phase distribution image, an image region having a phase amount that is not less than the threshold;
      generate first information distinguishing the phase distribution image from the image region;
      generate evaluation information indicating an extent to which the pluripotent stem cell remains pluripotent, the evaluation information being generated based on the first information; and
      output, via the communication unit, the evaluation information to an image display medium so as to display the evaluation information on the image display medium.

15. A microscope system comprising:
    a microscope configured to convert a phase distribution into an image intensity distribution;
    a display; and
    a computer communicably connected with the microscope and the display, the computer being configured to:
      form a phase distribution image of a pluripotent stem cell from images of the pluripotent stem cell, the images of the pluripotent stem cells being captured using the microscope and received from the microscope;

set, as a threshold, a phase amount of a mitochondrion in a somatic cell;
extract, from the phase distribution image, an image region having a phase amount that is not less than the threshold;
generate first information distinguishing the phase distribution image from the image region;
generate evaluation information indicating an extent to which the pluripotent stem cell remains pluripotent, the evaluation information being generated based on the first information; and
output the evaluation information to the display so as to display the evaluation information on the display.

* * * * *